United States Patent
Tomita et al.

[11] Patent Number: 6,004,351
[45] Date of Patent: Dec. 21, 1999

[54] PROSTHETIC KNEE JOINT

[75] Inventors: Naohide Tomita, Mie; Eijiro Ishikawa; Yoshiharu Asai, both of Tokyo, all of Japan

[73] Assignee: Mizuho Ika Kogyo Kabushiki Kaisha, Tokyo, Japan

[21] Appl. No.: 08/929,892

[22] Filed: Sep. 15, 1997

[30] Foreign Application Priority Data

Sep. 14, 1996 [JP] Japan .................................. 8-265207
Sep. 17, 1996 [JP] Japan .................................. 8-244752

[51] Int. Cl.⁶ .......................................................... A61F 2/38
[52] U.S. Cl. .................................................................. 623/20
[58] Field of Search .................................................. 623/20

[56] References Cited

U.S. PATENT DOCUMENTS

| | | |
|---|---|---|
| 5,007,933 | 4/1991 | Sidebotham et al. . |
| 5,035,700 | 7/1991 | Kenna ........................................ 606/88 |
| 5,358,530 | 10/1994 | Hodorek .................................... 623/20 |
| 5,387,240 | 2/1995 | Pottenger ................................. 623/20 |
| 5,609,639 | 3/1997 | Walker ..................................... 623/20 |
| 5,800,552 | 9/1998 | Forte ........................................ 623/20 |
| 5,824,100 | 10/1998 | Kester ...................................... 623/20 |
| 5,824,103 | 10/1998 | Williams ................................... 623/20 |

FOREIGN PATENT DOCUMENTS

| | | |
|---|---|---|
| 3-195549 | 8/1991 | Japan . |
| 3-195550 | 8/1991 | Japan . |
| 3-195551 | 8/1991 | Japan . |
| 3-267055 | 11/1991 | Japan . |
| 5-68987 | 9/1993 | Japan . |
| WO 95/14444 | 6/1995 | WIPO . |

*Primary Examiner*—Michael J. Milano
*Attorney, Agent, or Firm*—Kubovcik & Kubovcik

[57] ABSTRACT

A prosthetic knee joint enabling high-angle flexion includes the following members (a)–(c).

(a) a femoral component which is adapted to be secured to a distal femur, consists of implant metal, has a concave portion with a depth of 10 mm or more on the lower central surface thereof, adapted to be in slidable contact with the patella or a patellar component, and has a pair of spaced bearing surfaces spaced by the concave portion, consisting of an anterior erect portion, a lower portion and a posterior erect portion, which portions form a smoothly curved surface;

(b) a tibial component adapted to be secured to a proximal tibia, consists of implant metal and has an upper convex surface;

(c) a unitary bearing insert which consists of polyethylene, is situated slidably between the femoral component and the tibial component in use, has an upper concave surface for supporting the spaced bearing surfaces of the femoral component, defined between an anterior end and a posterior end and having a curvature radius within the range of from 20 mm to 1000 mm on the entire surface between the anterior and posterior ends, and also has a convex lower surface.

10 Claims, 17 Drawing Sheets

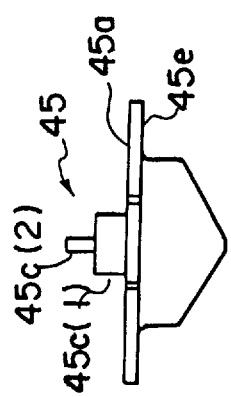
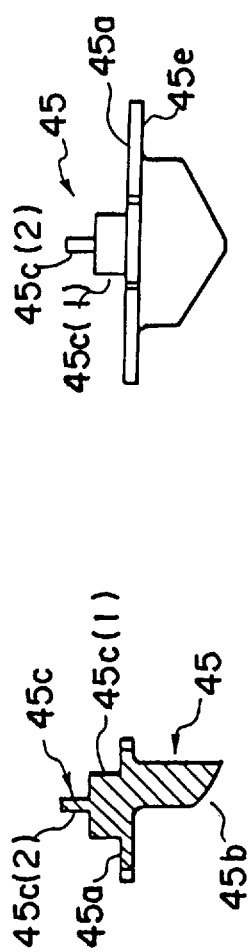
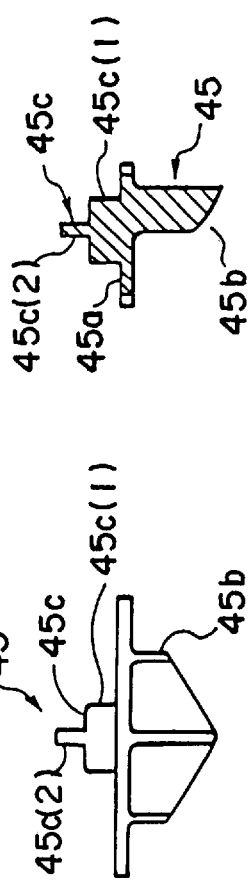
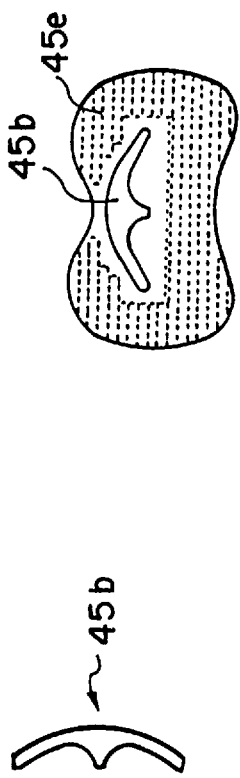
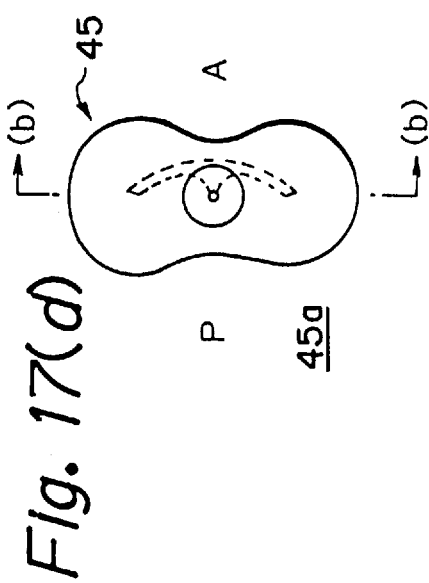
Fig. 17(a) Fig. 17(b) Fig. 17(c) Fig. 17(d)

PROSTHETIC KNEE JOINT

BACKGROUND OF INVENTION

Filed of Invention

The present invention relates to a prosthetic knee joint, more particularly, a prosthetic knee joint which enables high-angle flexion, has improved durability of the prosthetic components and also enhanced knee stability.

Knee arthroplasty, in which the natural knee is replaced with a prosthetic knee joint, is one of the most successful medical methods for remedying destructive knee-joint troubles.

U.S. Pat. No. 5,035,700 discloses a prosthetic knee joint which attains a high-angle flexion and is embodied, for example, as shown in FIG. 2, which schematically illustrates a fully flexed state. The prosthetic knee joint consists of a femoral component 1 consisting of implant metal, a tibial component 5 and a patellar component 20 consisting of plastics, e.g., polyethylene. The lower surface of the femoral component 1 is defined by the anterior erect portion 1a, the lower portion 1b and the posterior erect portion 1c, while each of these portions and the entire portions form a continuously smooth curved configuration. The femoral component 1 is provided with a peg 2 for securing it to the distal femur (not shown). The tibial component 5 has a concave surface 5a for enabling the femoral component 1 to slide thereon and is secured to the proximal tibia (not shown) with the stem 25.

The prosthetic knee joint proposed in the above mentioned U.S. Patent has a concave surface 1d at the lower central portion thereof, and the concave surface id is shaped to enlarge the maximum movement width of the prosthetic knee during flexion. It is described further the prosthetic components are configurated and dimensioned such that the quadriceps muscle tension approaches that in the natural human knee-joint throughout the full range of flexion.

Although not aiming at high-angle flexion, Japanese Examined Patent Publication No. 3-195,550 discloses the prosthetic components having virtually the same geometries as shown in FIG. 2.

The movement of the knee is not only a mere hinge action but also includes a swiveling action and a rolling action in the anterior and posterior direction. It additionaly includes a posterior rolling movement, which is essential in a high-angle full flexion, such that the contact between the femur and tibia displaces posteriorly and the axis of rotation also displaces posteriorly. Since the life style of Orientals frequently involves erect sitting position, the knee joint must be occasionally greatly flexed at high-angle flexion. It has been the practice to construct the prosthetic knee joint with an alumina femoral-component and a titanium-alloy tibial component with a bonded polyethylene top coating and to design the sliding surface between these components to enable high-angle flexion. However, when this prosthetic knee joint is fully flexed, the stress applied on the polyethylene top coating is greatly increased such that a danger arises of accelerated wear.

SUMMARY OF INVENTION

As is described hereinabove, a prosthetic knee joint, which enables high-angle flexion while attaining improved durability and which also attains enhanced knee stability, has not heretofore been provided.

It is, therefore, an object of the present invention to provide a measure to decrease the wear of polyethylene at a high-angle flexed state of a prosthetic knee joint, and hence to provide a prosthetic knee joint with improved reliability and performance.

In accordance with the objects of the present invention, there is provided a prosthetic knee joint enabling high-angle flexion (hereinafter referred to as "an implant-metal kneejoint") comprising:

a femoral component adapted to be secured to the distal femur, consisting of implant metal, having a pair of spaced bearing surfaces comprising an anterior erect portion, a lower portion and a posterior erect portion, which portions define a smoothly curved surface, and a central bearing surface adapted to be in slidable contact with the patella or a patellar component formed on a lower surface thereof, between the pair of the spaced bearing surfaces; and, a tibial component adapted to be secured to the proximal tibia, having an upper concave surface, and, a bearing insert consisting of polyethylene, situated slidably between the femoral component and the tibial component and having an upper concave surface and a lower convex surface.

According to an embodiment of the implant-metal kneejoint, a pair of bearing inserts consisting of polyethylene is situated slidably between the spaced bearing surfaces of the femoral component and the tibial component and has an upper concave and a lower convex surface.

In accordance with the present invention, there is also provided a prosthetic knee joint enabling high-angle flexion (hereinafter referred to as "the swivel-shaft knee joint"), comprising:

a femoral component adapted to be secured to the distal femur, consisting of implant metal, having a first concave bearing surface adapted to be in slidable contact with the patella or a patellar component, a second concave bearing surface, a pair of spaced portions spaced by the first and second concave bearing surfaces, and forming an anterior erect portion, a lower portion and a posterior erect portion, which portions form a smoothly curved surface, and a swiveling shaft secured between a pair of the spaced portions at a posterior end;

a tibial component adapted to be secured to the proximal tibia, consisting of implant metal and having an upper surface provided with a peg; and, an intermediate unitary component consisting of polyethylene, held by the peg of said tibial component and having a central upheaval portion formed on an upper surface thereof and being in slidable contact with the second concave bearing surface in use, a pair of spaced curved bearing surfaces, in slidable contact with the femoral component in use, formed on an upper surface thereof and spaced by the central upheaval portion, a generally L shaped step formed adjacent to the upheaval portion, and a bore on the lower surface for accommodating the peg therein; the pair of spaced portions of the femoral bearing and the spaced curved surfaces of the intermediate unitary component forming a sliding contact surface during flexion of the prosthetic knee joint, and said swivel shaft and said generally L shaped step cooperating together to smoothly swivel the swivel axis during a high-angle flexion of the prosthetic joint, and said intermediate unitary component being posteriorly inclined, when it being positioned essentially at the center of the tibial component viewed in the direction of flexion, such that a virtual line connecting the anterior and posterior ends of the spaced portions of the femoral component extends beneath a horizontal line across the anterior end of said spaced portions.

The patellar component may be made of polyethylene and have a shape as shown in FIG. 2.

There is also provided a prosthetic knee joint enabling high-degree flexion (hereinafter referred to as "the unitary concave bearing-insert knee joint") comprising:

a femoral component adapted to be secured to the distal femur, consisting of implant metal, having a concave portion with a depth of 15 mm or more, on the lower central surface thereof, adapted to be in slidable contact with the patella or a patellar component, and having a pair of spaced bearing surfaces spaced by the concave portion, consisting of an anterior erect portion, a lower portion and a posterior erect portion, which portions form a smoothly curved surface;

a tibial component adapted to be secured to the proximal tibia, consisting of implant metal and having an upper convex surface; and, unitary bearing inserts consisting of polyethylene, situated slidably between the femoral component and the tibial component in use, having upper concave surfaces for supporting the spaced bearing surfaces of the femoral component, defined between an anterior end and a posterior end and having a curvature radius within the range of from 20 mm to 1000 mm on the entire surface between the anterior and posterior ends, and also having a convex lower surface, said unitary bearing inserts being posteriorly inclined, when they are positioned essentially at the center of the tibial component viewed in the direction of flexion, such that a virtual line connecting the anterior and posterior ends of the spaced bearing surfaces forms an angle of from 1° to 25° between a perpendicular line across the longitudinal central axis of the tibial component.

There is also provided a prosthetic knee joint enabling high-angle flexion (hereinafter referred to as "the unitary flat bearing-insert knee joint") comprising:

a femoral component adapted to be secured to the distal femur, consisting of implant metal, having a concave portion with a depth of 15 mm or more, on a lower central surface thereof, adapted to be in slidable contact with the patella or a patellar component, and having a pair of spaced bearing surfaces spaced by the concave portion, consisting of an anterior erect portion, a lower portion and a posterior erect portion, which portions form a smoothly curved surface;

a tibial component adapted to be secured to the proximal tibia, consisting of implant metal and having an upper flat surface; and, unitary bearing inserts consisting of polyethylene, situated slidably between the femoral component and the tibial component in use, having an upper concave surface for supporting the spaced bearing surfaces of the femoral component, defined between an anterior end and posterior end with a curvature radius within the range of from 20 mm to 1000 mm on the entire surface between the anterior and posterior ends, and also having a flat lower surface, said unitary bearing inserts being posteriorly inclined, when they are positioned essentially at the center of the tibial component viewed in the direction of flexion, such that a virtual line connecting the anterior and posterior ends of the spaced bearing surfaces forms an angle of from 1° to 25° between a perpendicular line across the longitudinal central axis of the tibial component.

DESCRIPTION OF PREFERRED EMBODIMENTS

When the prosthetic knee joint according to the conventional architecture is fully flexed at a high angle, the convex surface of femoral polyethylene component and the flat surface of the implant-metal component are brought into contact at a very narrow area. The polyethylene is, therefore, liable to wear off and fatigue, while the flexing continues under the posterior rolling mechanism.

In the implant-metal knee joint and the unitary concave or flat knee-joint, the bearing insert consisting of polyethylene is slidably sandwiched between the femoral component and the tibial component, so as to eliminate the drawbacks of the conventional prosthetic knee joint.

When the implant-metal knee-joint is highly flexed at an angle of from approximately 150 to 170°, the contact between the femoral component and the bearing insert is displaced, posteriorly, and the rotational axis of flexion is also displaced posteriorly, along with the increase in the stress. After such posterior displacement, the stress decreases. The stress exerted on the bearing insert accordingly decreases. Subsequently, when the flexion angle is decreased from the maximum flexion angle amounting to approximately 170° during extension of the knee, a phenomenun opposite to the above described one occurs, so that the bearing insert is displaced posteriorly and is reverted to the original fully extended position.

It is preferred for the purpose of attaining a smooth sliding movement of the bearing insert between the femoral and tibial components that the following geometries (1)–(3) be adopted.

(1) The upper surface of a tibial component is concave, its radius of curvature is in the range of from 20 to 1000 mm on the entire surface. The upper surface of the tibial component is posteriorly inclined such that a virtual line connecting the anterior and posterior ends of the upper surface is inclined at an angle of from 1° to 25° downward below a line perpendicular to the central vertical axis of the tibial component.

(2) The posterior erect portion of the femoral component has a large bulge.

(3) The femoral component is deeply convex on its lower central surface so as to enable sliding on the patella thereon.

As is described above, when the prosthetic knee joint according to the conventional architecture is fully flexed at an angle of 150 to 170°, the polyethylene is liable to wear off and to fatigue due to contact at a narrow contact surface. The counter measure against this drawback according to the swivel-axis knee joint resides in the points (a)–(c).

(a) The femoral component is provided with a swivel axis which is smoothly swiveled and slides on the intermediate unitary component at a highly flexed state.

(b) The intermediate unitary component is provided with a bore on the lower surface for inserting the peg.

(c) The intermediate unitary component is provided with spaced sliding surfaces and a central upheaval sliding surface, for providing a sliding surface of the femoral component. These measures (a) through (c) are described successively.

Regarding measure (a), the swivel shaft, which is a secured part of the femoral component, undergoes a swiveling state, preferably under a flexion state of aproximately 90° or more. The swiveling shaft is supported, during swiveling around its central axis, on the generally L-shaped step of the intermediate component. The femoral component as a whole thus rotates until a flexion angle of approximately 170°. While the swivel shaft is in contact with smooth surfaces of the generally L-shaped step, the sliding continues until the intended high flexion angle is attained. The generally L-shaped step for enabling sliding of the swivel shaft according to the present invention is preferably formed between a pair of the spaced bearing surfaces of the femoral component.

Next, regarding (b), the intermediate component is held by the peg of the tibial component, in a fixed position notwithstanding flexion of the prosthetic knee joint. The intermediate component can, therefore, resist the forward pressure from the swivel shaft resulting in disengagement. The peg allows, however, a displacement around the femoral and tibial axial lines during the flexion of knee. The intermediate unitary component slides, therefore, on the tibial component in a rotary direction around the axis of the bore, so that the wear of polyethylene at high flexion angle can be mitigated.

Finally regarding the measure (c), the femoral component has, between a pair of the spaced portions, a sliding surface, on which the patella or patellar component slides, and another sliding surface, on which the central upheaval portion of the intermediate portion slides. The contact areas between the femoral and intermediate unitary component under a middle or highly flexed state are, therefore, a contact area between the spaced portions of the two components and a contact area between the central upheaval portion and said another sliding surface of the femoral component. As a result, the sliding pressure is maintained at such a low level that the wear of polyethylene is greatly reduced.

The femoral component has, therefore, according to the present invention ($s_1$) a sliding surface, on which the patella or patellar component slides, ($s_2$) an intermediate sliding surface, and, ($s_3$) a generally L shaped step formed successively in the posterior direction. The angle of flexion, in which the generally L shaped step ($s_3$) mentioned above participates, is from approximately 90° to 170°. The posterior region of the surface ($s_1$) (high flexion-angle region) and the anterior region of the surface ($s_2$) (low flexion-angle region) may overlap with one another, so that the patella and then the intermediate unitary component slide on the overlapping region of the femoral component, at a relatively low angle of flexion, e.g., 50°, and a relatively high angle of flexion e.g., 130°, respectively. As in the ordinary description of the prosthetic knee joint, the anterior end indicates a portion, where the patella or patellar component is first brought into contact.

Furthermore, the above-mentioned geometries (1) through (3), can be applied in the swivel-axis knee-joint so as attain a smooth sliding movement of the intermediate component and the femoral and tibial components and to increase flexion angle.

In the unitary concave or flat bearing-insert knee joints, the above measures (1) through (3), (b) and (c) are applied to attain high flexion-angle.

BRIEF DESCRIPTION OF DRAWINGS

FIG. 15(*a*) is a side elevational view. FIG. 15(*b*) is a front view. FIG. 15(*c*) is a rear view.

FIG. 16(*a*) is a side elevational view. FIG. 16(*b*) is a cross sectional view along the line (b)—(b). FIG. 16(*c*) is a cross-sectional view along the line (c)—(c). FIG. 16(*d*) is a plan view.

FIGS. 17(*a*)–17(*d*) are drawings showing an embodiment of the tibial component. FIG. 17(*a*) is a side elevational and partly cross sectional view. FIG. 17(*b*) is a cross sectional view along the line (b)—(b). FIG. 17(*c*) is a front view. FIG. 17(*d*), is a plan view.

FIG. 27(*a*) is a plan view. FIG. 27(*b*) is a cross sectional view along the line (b)—(b).

The implant-metal knee-joint according to the present invention is hereinafter described with reference to FIG. 1. The femur, the tibia and the bearing insert are denoted as 3, 4 and 6, respectively. The bearing insert 6 consists of polyethylene and is slidably sandwiched between the femoral component 1 and the tibial component 5, each consisting of implant metal. In the extended state shown in FIG. 1, the femoral component 1 pushes slightly posteriorly the bearing insert 6 supported on the slanting surface of the tibial component 5.

Figure 3:
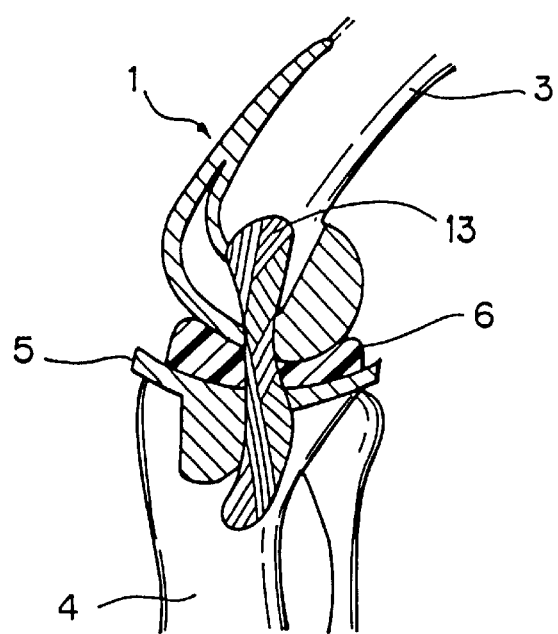
FIG. 3 shows the prosthetic knee joint according to the present invention, flexed at an angle of flexion of 30°.
Figure 4:
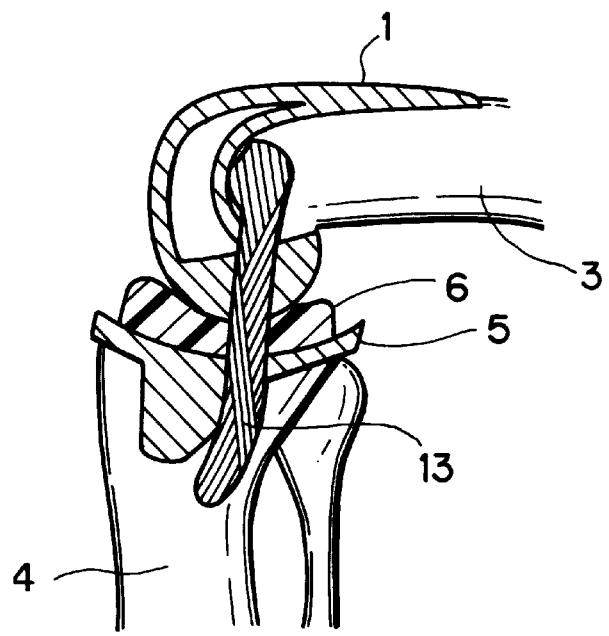
FIG. 4 is a drawing similar to FIG. 3, at an angle of flexion of 90°.
Figure 5:
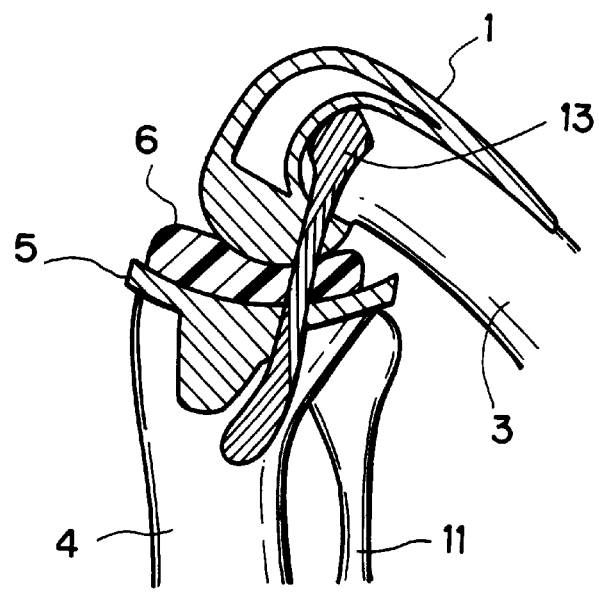
FIG. 5 is a drawing similar to FIG. 3, at an angle of flexion of 130°.

FIGS. 3 through 5 schematically illustrate the flexion of the knee. The flexion angle is from 90 to 130° in FIGS. 4 and 5. Along with the flexion, the bearing insert 6 is caused to slide on the tibial component 5 due to frictional force between the femoral component 1 and the bearing insert 6, so that the bearing insert 6 reaches a position where the tension of the accessory ligament of the knee is mitigated.

The upper surface of the bearing insert 6 forms an arc or smoothly connected continuous arcs having a curvature radius of from 20 to 1000 mm. Therefore, when an axial load caused by human weight is applied to the bearing insert 6, it is displaced to a stable position, thereby enabling stable walking even if the peripheral structure is fragile. Either in a case that the radius of curvature is less than 20 mm or more than 1000 mm, the contact area between the femoral component 1 and the bearing insert 6 is disadvantageously narrow. The curvature of radius is preferably from 20 to 100 mm.

Figure 7:
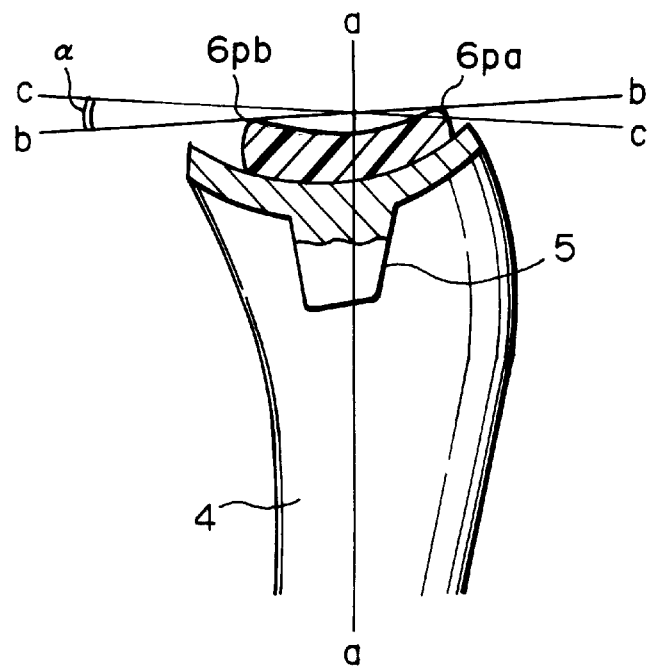
FIG. 7 is a drawing illustrating the tibial component.
Figure 8:
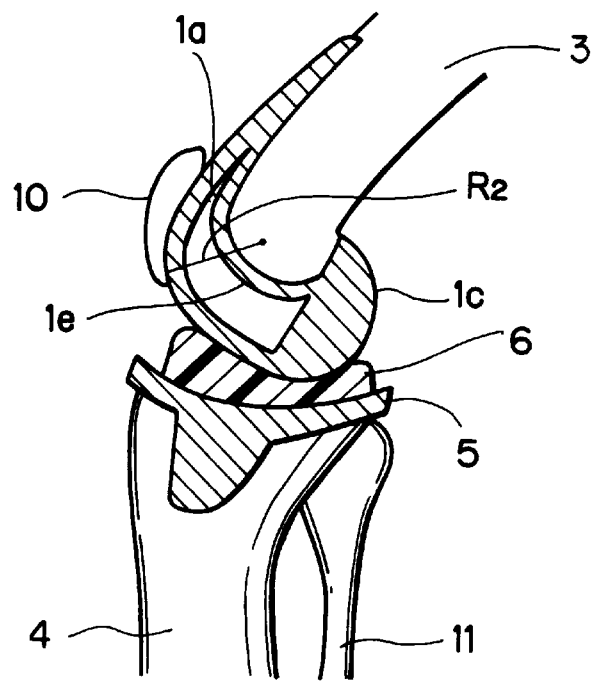
FIG. 8 illustrates another embodiment of the prosthetic knee joint different from the one illustrated in FIG. 1.

The inclined location of the bearing insert 6 is determined as follows as described with reference to FIG. 7. In FIG. 7, the line a—a is a tibial central axial line extending along virtually the center of the tibia 4. The plane c—c intersects perpendicularly the line a—a. The line b—b connects the anterior end 6 pa and the posterior end 6 pb of the bearing insert 6. The angle (α) defined between the plane c—c and the line b—b extending beneath the plane c—c is set in the range of from 1 to 20° according to the present invention, thereby realizing smooth sliding of the bearing insert 6.

Figure 6:
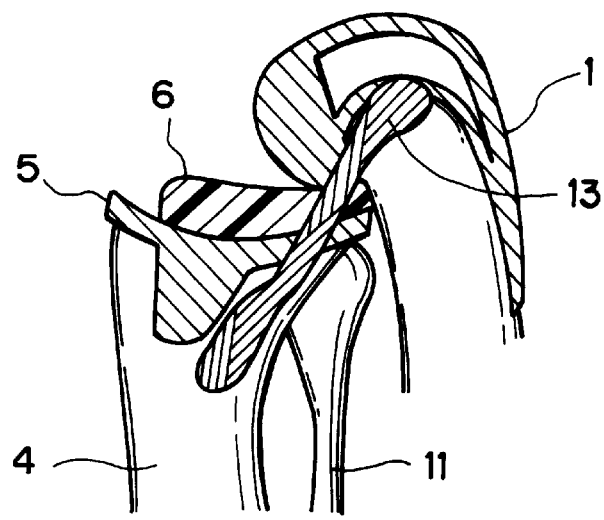
FIG. 6 is a drawing similar to FIG. 3, at an angle of flexion of 170°.

When the flexion angle increases from 130° to 170°, since the posterior rolling movement occurs as illustrated in FIGS. 5 and 6, the contact region between the femoral component 1 and the bearing insert 6 is displaced posteriorly, while the bearing insert 6 slidably sandwiched between the components 1 and 5 is also displaced backward on the tibial component 5. Along with such displacement, the bearing insert 6 undergoes friction with respect to the components 1 and 6. This wear is considerably slight and of almost negligible extent as compared with that of the conventional stationary prosthetic knee joint, where the local stress is greatly increased during the flexion.

Furthermore, since the femoral component 1 according to the present invention has a posterior erect portion 1c (FIG. 1) with a bulge, the femoral component 1 and the bearing insert 6 can maintain a smooth sliding surface even at a high-angle flexion of 170° or more. The posterior erect portion 1c (FIG. 1) preferably has a thickness of 15 mm or more, more preferably 20 mm or more.

Figure 9:
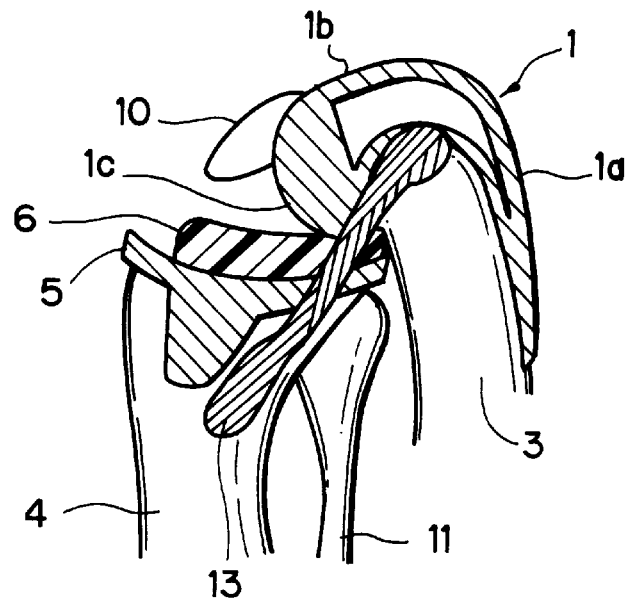
FIG. 9 is a drawing similar to FIG. 8, at an angle of flexion of 170°.
Figure 10A:
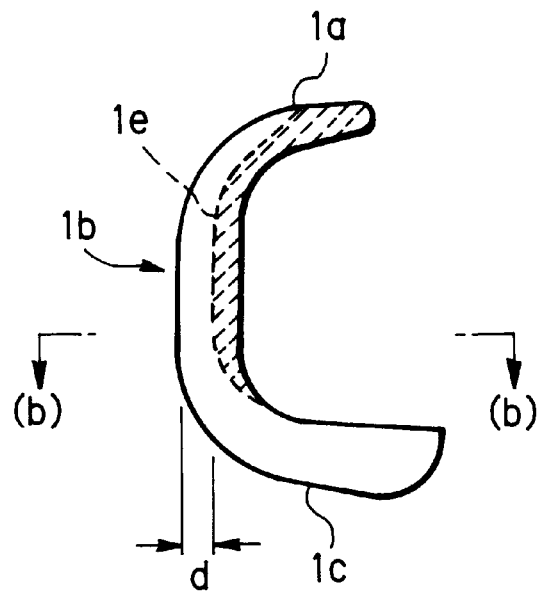
FIG. 10(*a*) is a side elevational view of a femoral component and FIG. 10(*b*) is a cross-sectional view along the line (b)—(b) of FIG. 10(*a*).
Figure 10B:
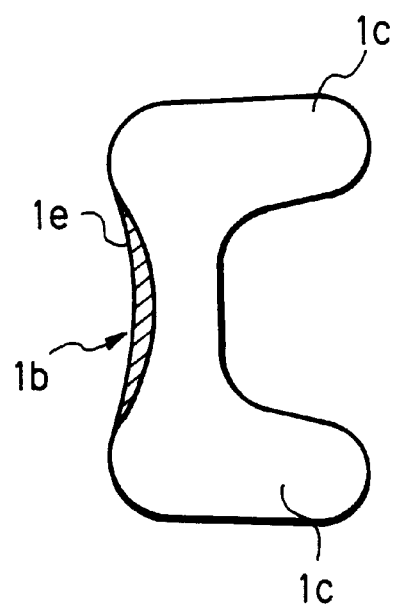

Under a high-angle flexion state shown in FIG. 9, the pressure between the patella 10 and the femoral component 1 can be decreased by means forming on the central region of the lower portion 1b a deep concave bearing surface 1e (FIG. 10) with a depth (d)=10 mm or more for providing the sliding surface of the patella 10.

Figure 11:
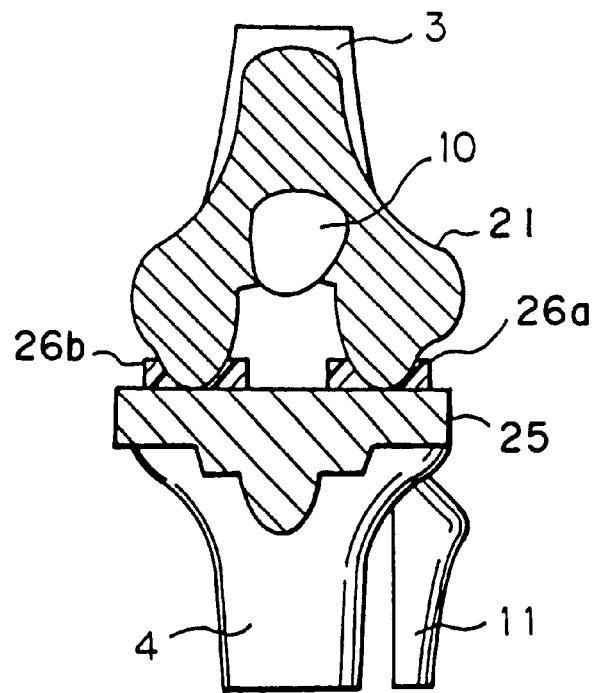
FIG. 11 illustrates a preferred embodiment of the implant metal knee joint.
Figure 12:
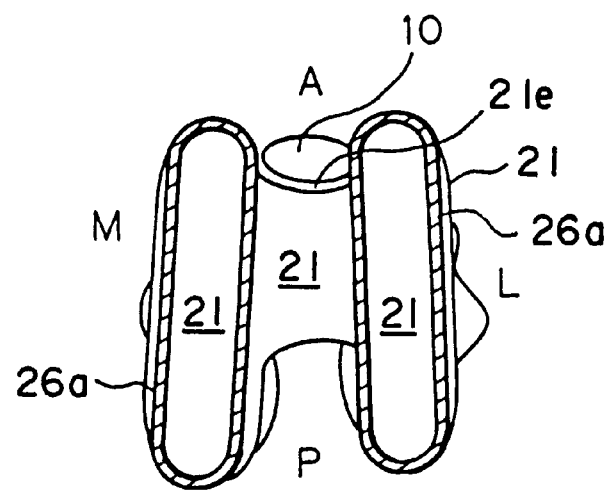
FIG. 12 is a bottom view of the femoral component shown in FIG., 11.

An embodiment of the implant-metal knee-joint is illustrated in FIGS. 11 and 12. As shown in FIG. 11, the femoral component 100 has, at its lower and posterior erect portions, a generally inverse U shape. The base of the inverse U shape, from which the spaced portions split, provide the bearing surface of the patella. The front spaced portions of the inverse U shape provide bearing surfaces of the bearing inserts 26a, 26b.

Furthermore, as shown in FIG. 12, the inter-spacing between a pair of the bearing inserts 26a, 26b is more enlarged at a position closer to the posterior (P). The bearing inserts 26a, 26b are therefore spread laterally along with the flexion of knee, thereby preventing the bearing inserts 26a, 26b from disengagement.

Figure 13:
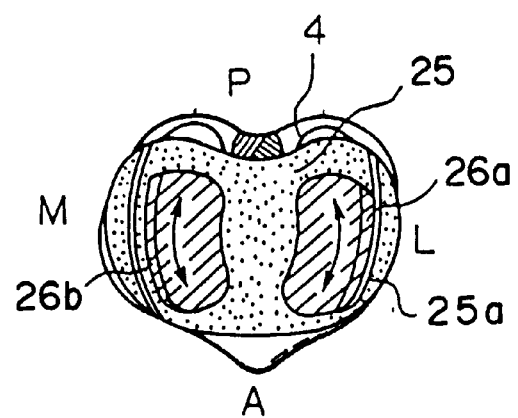
FIG. 13 is a plan view of FIG. 11 as viewed from the top surface of the bearing inserts.
Figure 14:
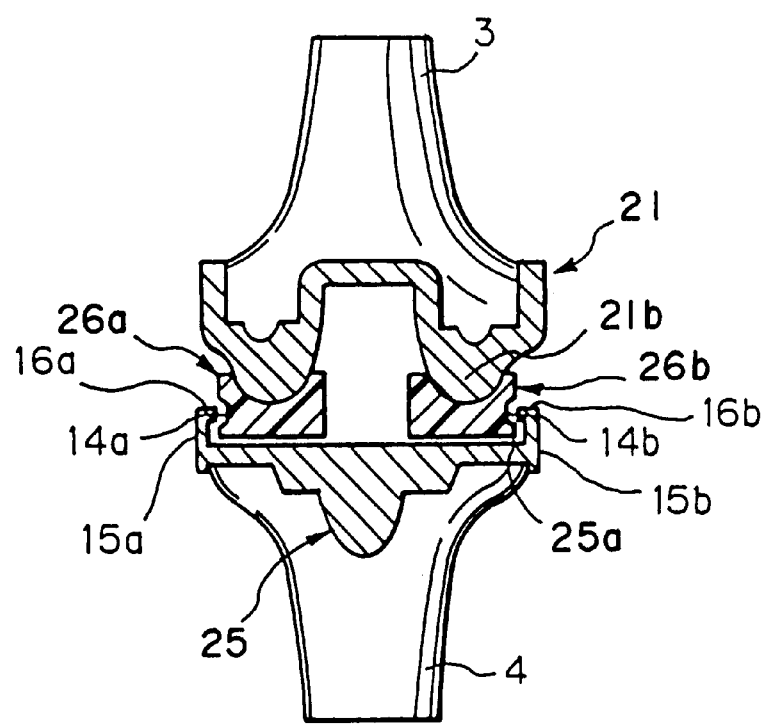
FIG. 14 is a front view of FIG. 13 and cross sectional view of the prosthetic components.

Referring to FIGS. 13 and 14 there is shown another embodiment of the implant-metal knee-joint. The bearing inserts 26a, 26b slide in the direction indicated in FIG. 13 by arrows. This direction is a composite of two directions, i.e., mainly an anterior-posterior (A-P) direction and slightly mediallateral (M-L) direction. The bearing inserts 26a, 26b are, therefore, designed slightly shorter, for example, 1 mm to 20 mm than the length of the tibial component 25.

The bearing inserts 26a, 26b have grooves 14a, 14b on the lateral sides, extending longitudinally, i.e., the direction vertical to the drawing plane of FIG. 14. Lugs 16a, 16b which are formed on upward extensions 15a, 15b from both sides of the tibial component 25, engage the grooves 14a, 14b. When the flexion angle is so increased as to force the bearing inserts 26a, 26b laterally (L, M), the lugs 16a, 16b enter the grooves 14a, 14b, and the bearing inserts 26a, 26b are then pushed against the frame portion of the tibial component 25, thereby preventing the bearing inserts 26a, 26b from disengagement at a high angle of flexion. Note, that a clearance is formed between the bearing inserts 26a, 26b and the upward extensions 15a, 15b under the extended state of the knee.

Figure 15A:
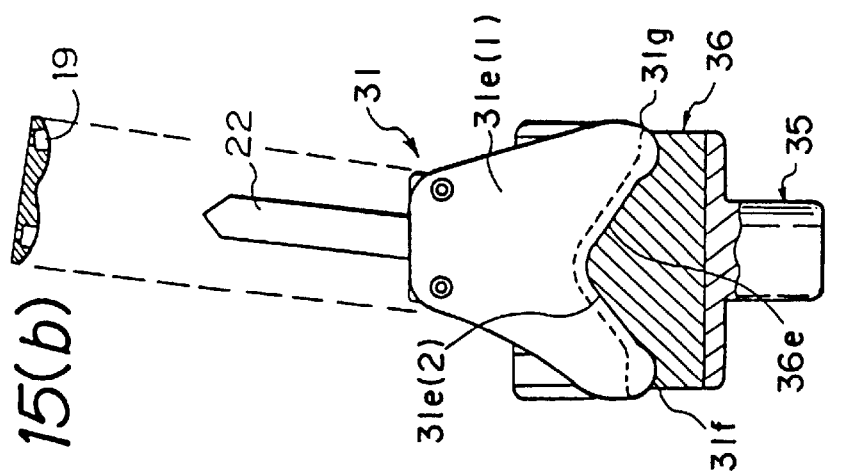
FIGS. 15(*a*)–15(*c*) are drawings showing an embodiment of the swivelaxis knee joint.
Figure 15B:
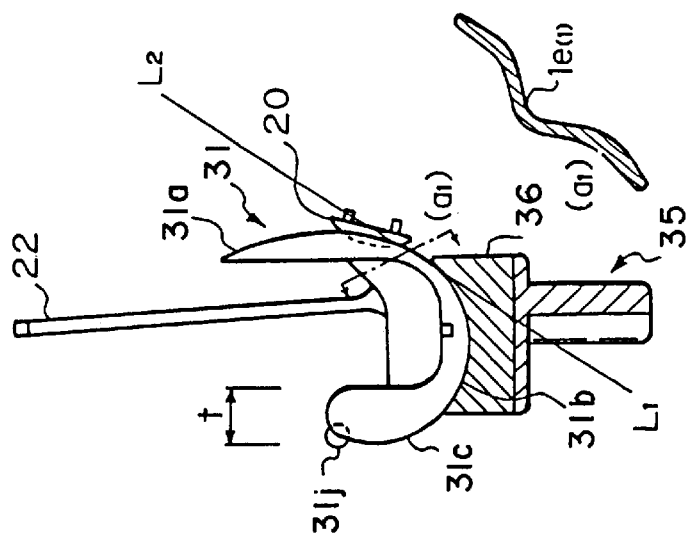
Figure 15C:
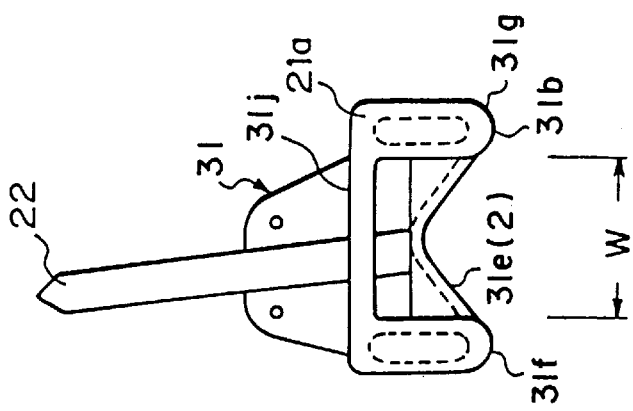
Figure 16B:
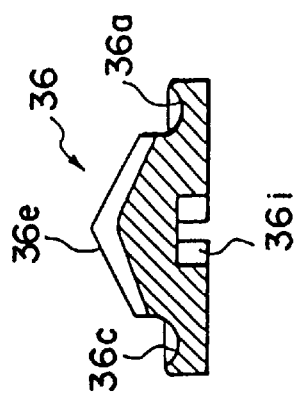
FIGS. 16(*a*)–16(*d*) are drawings showing an embodiment of the intermediate component.
Figure 16A:
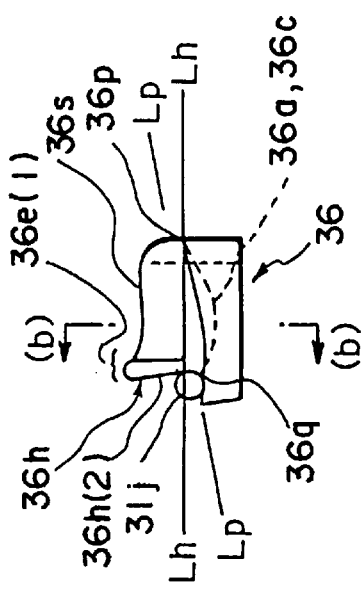
Figure 16D:
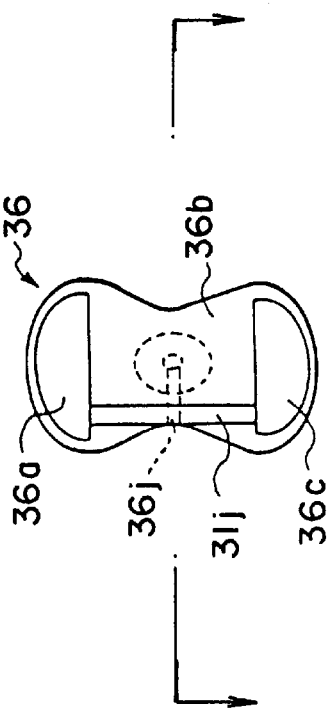
Figure 16C:
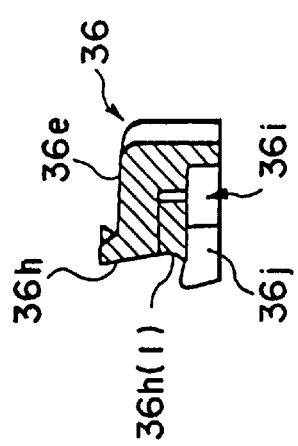

Now, an embodiment of the swivel-axis knee-joint is described with reference to FIGS. 15 to 18. FIGS. 15(a) and 15(b) are an overall side view and front view of the swivel-axis knee joint, respectively. FIG. 15(c) is a rear view of the femoral component. FIGS. 16(a), (b), (c) and (d) are a side view, a cross-sectional view along the line (b)—(b), a longitudinal cross sectional, and a plan view of the intermediate unitary component, respectively. The intermediate unitary component is denoted as 36, consists of polyethylene and is sandwiched between the femoral component 31 and tibial component 35, each made of implant metal.

The surfaces of the femoral component 31 sliding on the intermediate unitary component 36 are the anterior erect portion 31a, the lower portion 31b and the posterior erect portion 31c, as well as the peripheral surface of the swivel axis 31j. The portions 31a through 31c form a gentle curved surface (c.f., FIG. 15(a)). The patellar component 20 slides on the first concave portion $31e_{(1)}$ (FIGS. 15(a) and (b)). The spaced portions (31f, 31g), which are spaced from one another by the concave portion $31e_{(1)}$, are formed and define the anterior erect portion 31a, the lower portion 31b and the posterior erect portion 31c, each being the sliding surface of the intermediate unitary component 36. The spaced portions 31f, 31g are hollow in light of weight reduction (c.f. FIG. 15(c)). The second concave portion $31e_{(2)}$ is in contact with the central upheaval portion 36e of the intermediate unitary component 36 in FIG. 15(b). The second concave portion $31e_{(2)}$ is formed behind the first concave portion $31e_{(1)}$ and is in contact with essentially the entire surface of the central upheaval portion 36e of the intermediate unitary component during sliding.

The line $L_1$–$L_2$ in FIG. 15(a) is a tangential line of the most external surface of the femoral component 31, where the first and second concave surfaces $31e_{(1)}$ and $31e_{(2)}$ (FIG. 15(b)) are formed. The depth of the first and second concave surfaces $31e_{(1)}$ and $_{(2)}$, are measured by the length of a line segment vertical to the line $L_1$–$L_2$. The maximum depth of the first and second concave surfaces $31e_{(1)}$ and $31e_{(2)}$ is preferably 15 mm or more. The width (W) of these concave surfaces measured by the distance between the lower apexes of the spaced portions 31f, 31g is preferably 35 mm or more and more than 58% of the lateral width of the prosthetic knee joint. The depth of these concave surfaces is preferably 10 mm or more.

Figure 18:
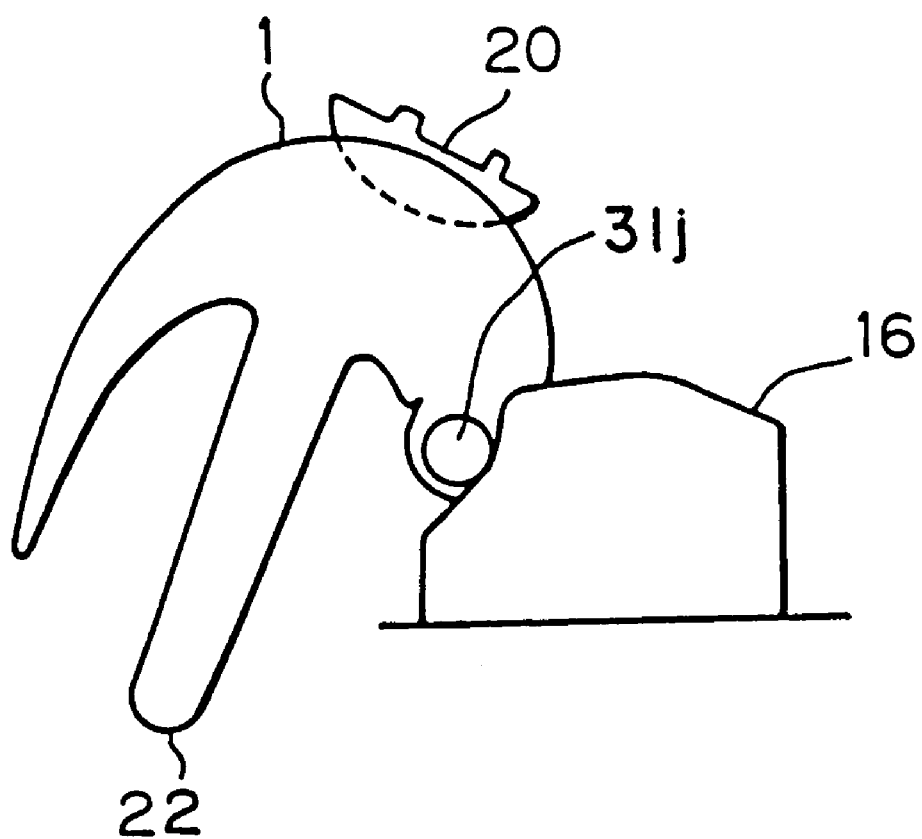
FIG. 18 illustrates the flexion at an angle of 170' of the swivel-axis knee-joint.

The swiveling shaft 31j is secured to and extends between the ends of the spaced portions 31f, 31g and assists the posterior rolling movement in such a manner to decrease the wear of polyethylene at a high-angle flexion state. The swiveling shaft 31j is not brought into contact with any portions of the intermediate unitary component 36 under the extended state shown in FIG. 15(a). When the flexion angle increases, the swivel shaft 31j abuts on the intermediate unitary component 36 and the femoral component 31 is then swiveled concentrically around the swiveling shaft 31j until flexing approaches the erect sitting position as shown in FIG. 18. The swiveling shaft 31j may not abut on the generally L-shaped step formed behind the central upheaval portion 36e but may abut on the spaced curved portions 36a, 36c of the unitary bearing insert 36 behind the above-mentioned step. It is, however, preferable that the swivel shaft 31j abuts on the step 36h formed behind the central upheaval portion 36e as shown in FIG. 16(a).

The patellar component 20 has preferably a thickness in the range of from 2 to 35 mm. When the thickness is great within this range, a high-angle flexion becomes easy. On the other, hand, when the thickness is small within this range, flexion force becomes high.

A pair of spaced curved bearing surfaces 36a and 36c of the intermeidate unitary component 36 guides, during the flexion, the spaced portions 31f and 31g (FIGS. 15(b) and (c)). The curvature radius of the spaced curved bearing surface 36a or 36b is virtually coincident with that of the spaced portion 31f or 31g, as viewed both in the front-rear direction and the lateral direction. Their (31f, 31g, 36a and 36c) contact area is therefore large, which also contributes to decrease the wear of polyethylene. In addition, since the central upheaval portion 36e is a sliding surface of the femoral component 31, the contact pressure can be further decreased and the wear of polyethylene is hence further decreased.

The spaced curved bearing surfaces may be formed on mutually separate bodies, that is, a pair of the intermediate components are provided. However, since a pair of the intermediate components is not only difficult to place surgically but also may be disengaged after placement and is of poor stability, the spaced curved bearing surfaces are, therefore, preferably mutually constrained and unitary, specifically, as shown in FIG. 16.

As is described hereinabove, smooth sliding movement of the swiveling shaft 31j in the circumferential direction is attained by the generally L-shaped step 36h (FIG. 16), which is formed adjacent to the central upheaval portion 36e. The swiveling shaft 31j is supported on the basal surface $36h_{(1)}$ of the generally L-shaped step 36h as follows. When the flexion advances to such an extent that the contact area between the second concave surface $31e_{(2)}$ (FIG. 15(c)) and the central upheaval portion 36e is so decreased that almost no contact occurs, the swiveling shaft 31j is supported on the step 36 as shown in FIG. 16(a). The sliding of the swiveling shaft 31j occurs on the basal plane $36h_{(1)}$ (FIG. 16(a)). The femoral component 31 swivels then concentrically around the swiveling shaft 31j. Since the vibration and swinging of the swiveling shaft 31j in the horizontal and vertical directions are extremely small, smooth sliding is realized. Preferably, as shown in FIG. 16(a), the generally L-shaped step 36h is defined by the erect portion $36h_{(2)}$, which slants inwardly in the direction of the swiveling shaft 31j at an opening angle of less than 90°, and an arcuate basal surface $36h_{(1)}$ having a curvature radius approximately equal to the radius of the swiveling shaft 31j. The arcuate basal surface $36h_{(1)}$ preferably contacts the arcuate region of swiveling shaft 31j having an angle of 60° to 100°. The contact pressure of the swiveling shaft 31j on the basal plane $36h_{(1)}$ can thus be decreased.

The spaced curved bearing surfaces 36a, 36c shown in FIGS. 16(b) and (d) are defined by a single arc or plurality of smoothly connected arcs, each arch having a curvature radius in the range of from 20 mm to 1000 mm, preferably from 20 mm to 100 mm, for the reasons as described with reference to FIGS. 1 and 2 through 6.

The central upheaval portion 36e is in slidable contact with the second concave surface $31_{(2)}$ (c.f., FIG. 15(b)) of the femoral component 31. The configuration of the central upheaval portion 36e as seen in the flexing direction is generally concave as shown in FIG. 16(a) so as to decrease the contact pressure from the femoral component 31 having a convex configuration in the flexing direction. The inclination of the central upheaval portion 36e is more increased in the rear side $36e_{(1)}$ with an increase in the flexing angle, so as to prevent disengagement at a high flexion angle.

Figure 1:
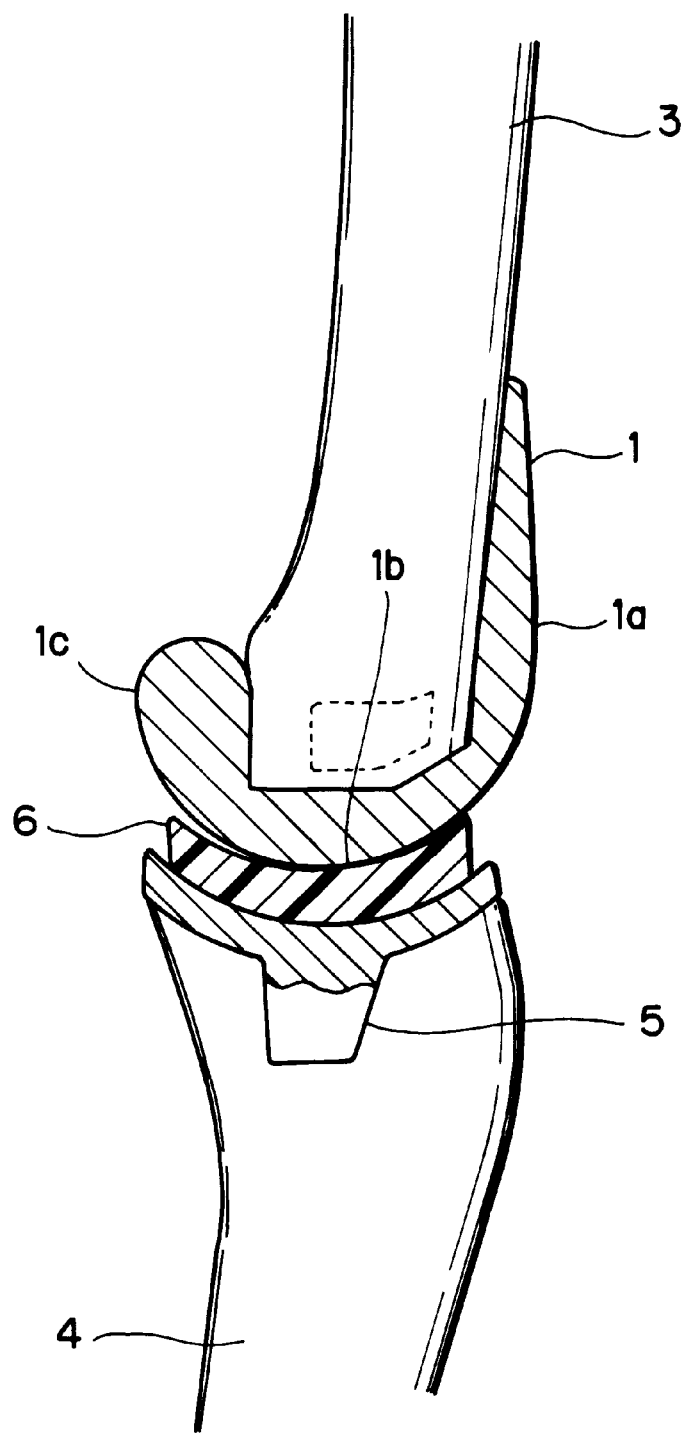
FIG. 1 is a side-elevational drawing illustrating an embodiment of the implant-metal knee-joint according to the present invention.
Figure 2:
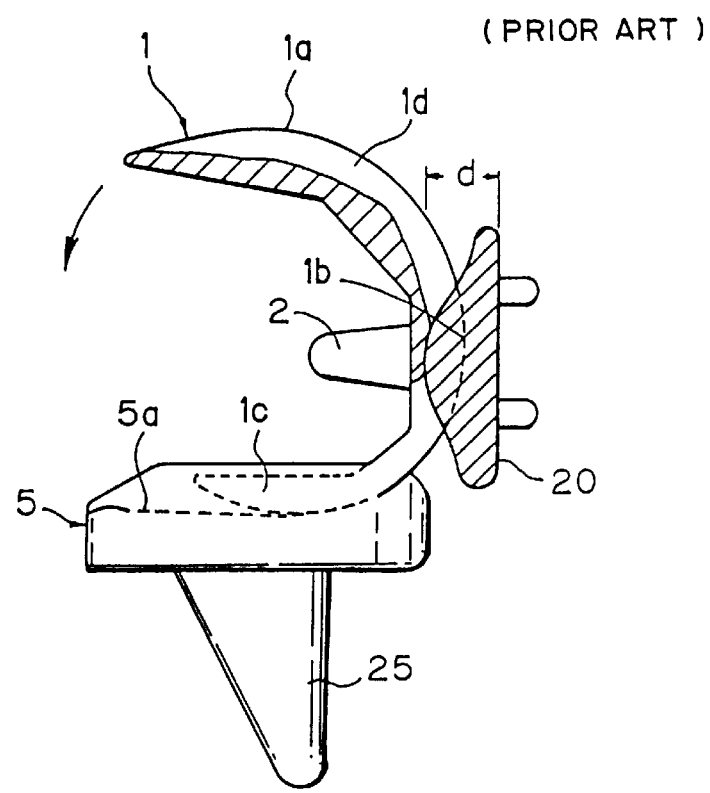
FIG. 2 illustrates an example of the conventional prosthetic knee joint.

The femoral component 31 may be provided with tap holes 19 (FIG. 15(b)) for securing the femoral component 31 to the femur 3 (FIG. 1).

Reference numeral 36i (FIG. 16) denotes the bore which enables the fitting of the intermediate unitary component 16 and the tibial component 35 (FIG. 15(a), (b)), for preventing the former component 36 from disengagement. In addition, the bore 36i enables a relative angular rotation of both components 36 and 35 and realizes, during the knee flexion, the displacement around the central shaft of the femur and tibia.

Reference numerals 36p and 36q shown in FIG. 16(a) denote the anterior and posterior ends of the spaced curved bearing surfaces 36a, 36c. The line $L_h$—$L_h$ is the horizontal line across the anterior end 36p, while the line $L_p$–$L_q$ is the line connecting the anterior end 36p and the posterior end 36q. The segment of line $L_p$-$L_q$ line above the spaced bearing surfaces 36a, 36c is inclined downward the horizontal line $L_h$—$L_h$ at an angle of preferably from 0 to 30°.

Referring to FIG. 17, another embodiment of a tibial component 45 is illustrated. FIGS. 17(a), (b), (c) and (d) are side elevational and partly cross sectional view, a cross-sectional view along the line (b)—(b), a front view, and plan view, respectively. The tibial component 45 has a sliding surface 45a, on which the intermediate unitary component slides. The tibial component 45 is also provided with a stem 45b and a peg 45c for preventing the intermediate unitary component from disengagement. The peg 45c consists of the base portion $45c_{(1)}$ having a diameter of preferably from 5 to 30 mm and having a height of preferably 5 to 30 mm, and an upper portion $45c_{(2)}$ having a diameter of preferably from 1 to 10 mm and having a height of preferably 5 to 30 mm. The preferable length of each portion $45c_{(1)}$ and $45c_{(2)}$ is from approximately 4 to 15 mm. The bore 36i (FIG. 16(c)) consists also of the portions corresponding to these portions $45c_{(1)}$ and $45c_{(2)}$.

Again reverting to FIG. 16(c), the intermediate unitary component 36 has on its bottom a recess 36j for guiding the peg 45c therethrough from the posterior side at insertion. That is, at operation, the femoral component must be lifted to form a clearance between the femoral and tibial components, so as to enable insertion of the intermediate unitary component 36. Since only the front tip portion $45c_{(2)}$ needs to pass through the recess 36j, the required lifting height can be diminished by the height of this portion $45c_{(2)}$.

Figure 19:
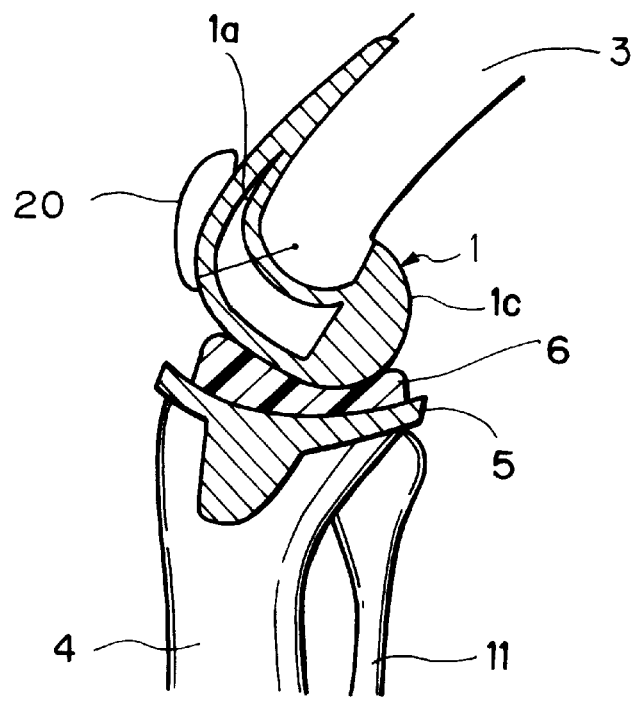
FIG. 19 is a side elevational-view of an embodiment of the implant-metal knee joint.
Figure 20:
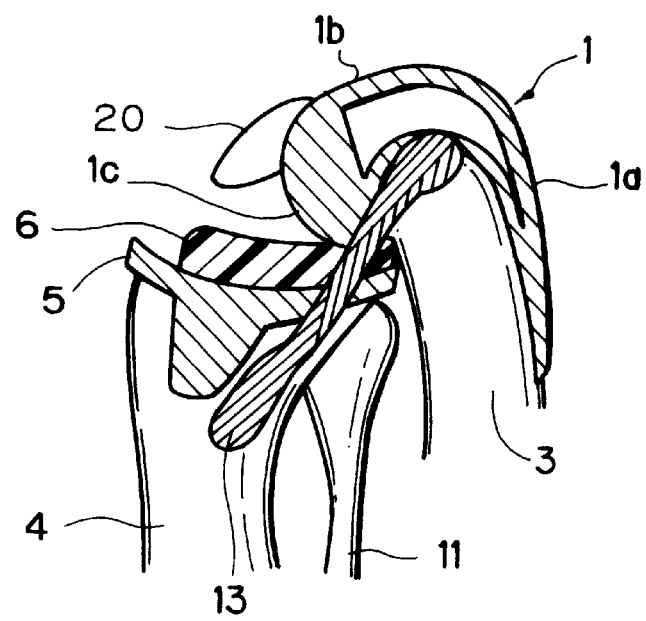
FIG. 20 is a drawing illustrating the flexion at an angle of 170° and sliding on the patellar component.
Figure 21A:
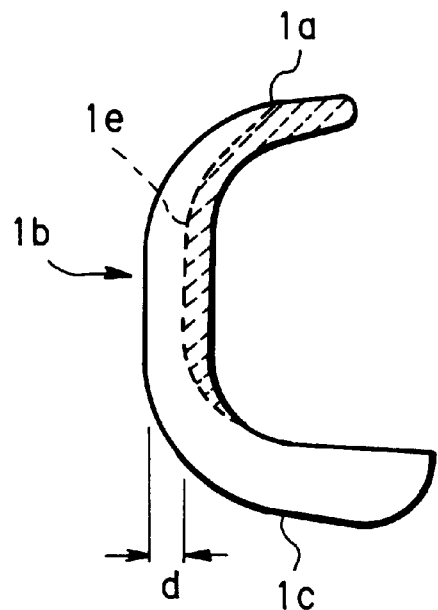
FIGS. 21(*a*) and 21(*b*) are a side view and a bottom view of the femoral component, respectively.
Figure 21B:
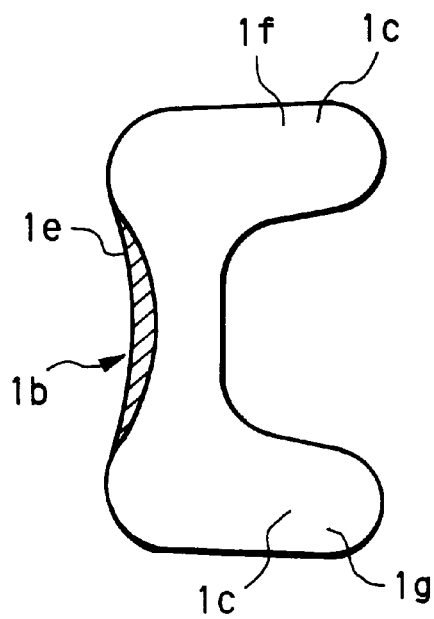

Now, the function of bulge of the posterior erect portion 1c is described with reference to FIGS. 19 and 20. When the flexing angle increases from that shown in FIG. 19 to 150°–170° (FIG. 20), the bulge of posterior erect portion ic maintains a smooth sliding surface on the bearing insert 5 or the intermediate unitary component. In order to maintain a low pressure between the patellar component 10 and the femoral component 1 under highly flexed state as shown in FIG. 20, the concave surface 1e (FIG. 21(a), (b)) of the femoral component 1 must be deep, particularly 10 mm or more, as described above. FIGS. 19 and 20 show that the patellar component 10 slides on the deep convex surface formed on the central front portion of the femoral component 1.

Figure 22:
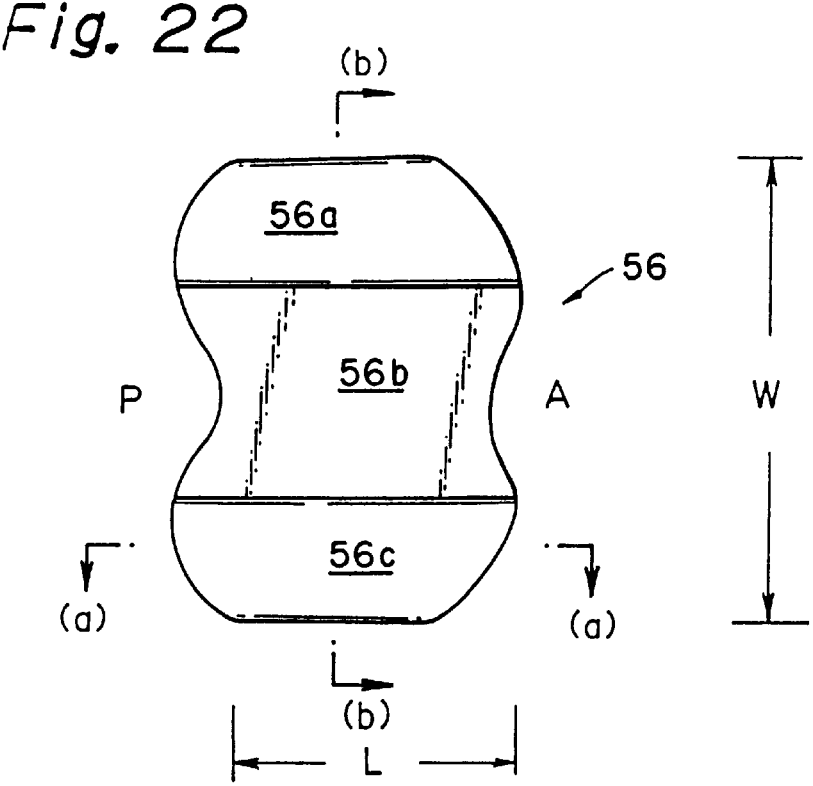
FIG. 22 is a drawing showing a preferred embodiment of the bearing insert according to the present invention.
Figure 23:
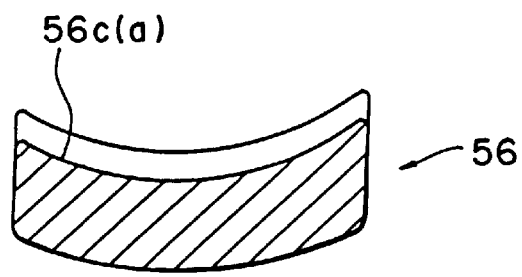
FIG. 23 is a cross-sectional drawing along the line (a)—(a) of FIG. 22.
Figure 24:
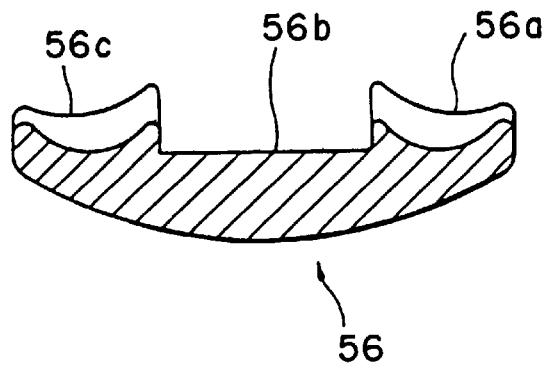
FIG. 24 is a cross-sectional drawing along the line (b)—(b) of FIG. 22.
Figure 25:
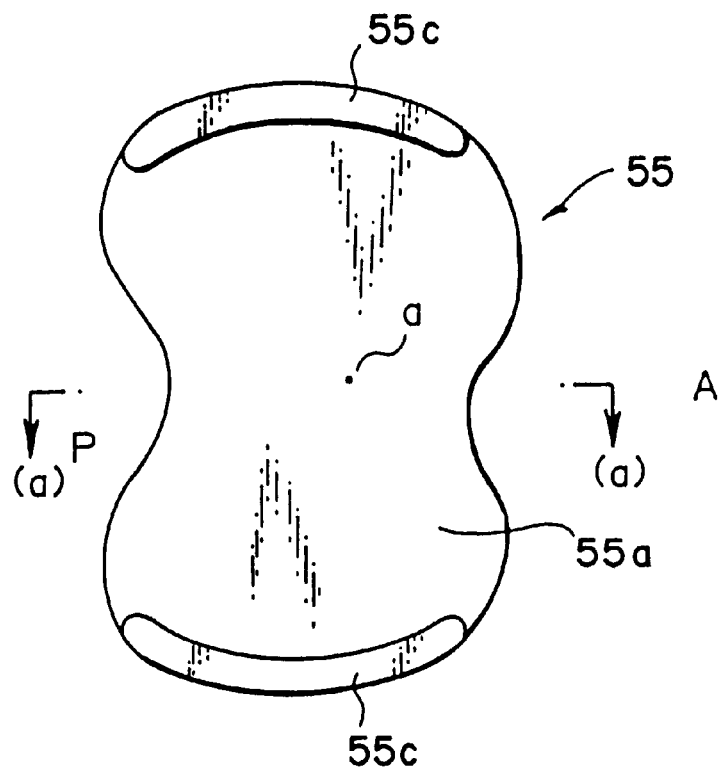
FIG. 25 is a plan view of the tibial component according to the unitary concave or flat bearing-insert knee-joint.
Figure 26:
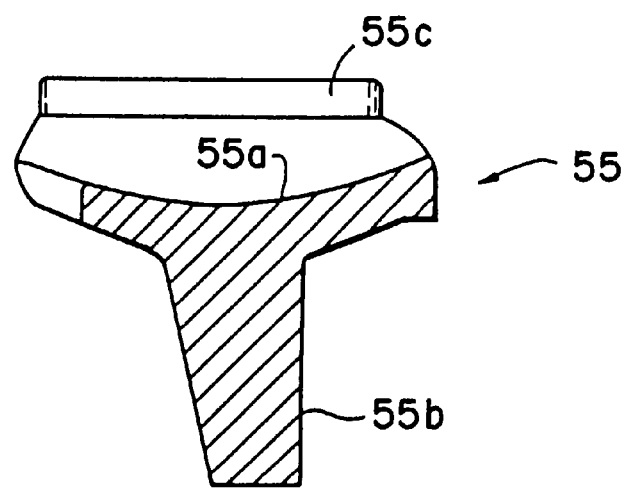
FIG. 26 is a cross sectional drawing along the line (a)—(a) of FIG. 25.

Now, an embodiment of the unitary concave bearing-insert knee joint is described with reference to FIGS. 22 through 26 and an embodiment of the unitary flat bearing-insert knee joint is described with reference to FIGS. 27 and 28. FIGS. 22, 23 and 24 are a plan view, a cross sectional view along the line (a)—(a), and a cross sectional view of the intermediate unitary component along the line (b)—(b), respectively. FIG. 25 and FIG. 26 are a plan view and a cross sectional view along the line (a)—(a) of the tibial component, respectively. The descriptions hereinabove made with reference to FIGS. 1, 3 through 6, and FIGS. 19 through 21 are also applied to these embodiments. The descriptions, hereinabove, of a specific component(s) with reference to the specified drawings below are also applied to these embodiments.

The bearing insert 46 (FIGS. 22–24) has a pair of spaced curved bearing surfaces 46a and 46c for guiding the spaced portions 31f and 31g of the femoral component (FIG. 15). The spaced portions 31f, 31g slide on the spaced curved bearing surfaces 56a, 56c in the flexing direction as shown in FIG. 23 and in the lateral direction as shown in FIG. 24. Radius of curvature of the spaced curved bearing surfaces 56a, 56c as shown either in FIG. 23 or 24 and that of the spaced portions 31f, 31g are virtually coincident, with the result their (31f, 31g, 56a and 56c) contact area is so large as to decrease the wear of polyethylene.

The spaced curved bearing surfaces 56a, 56c may be formed on mutually separate bodies, that is, a pair of bearing inserts is provided. However, since a pair of the bearing inserts is not only difficult to place surgically but also may be disengaged after placement and is of poor stability, the spaced curved bearing surfaces 56a, 56c are, therefore, preferably mutually constrained and unitary, specifically as shown in FIGS. 22 through 24. The unitary bearing insert 56 is not limited to the one shown in FIGS. 22 through 24 but may be embodied such that an aperture is formed through the intermediate portion 56b or the length (L) of the intermediate portion 56b (FIG. 22) is shortened to decrease the weight.

The tibial component 55 shown in FIGS. 25 and 26 has a bearing surface 55a, on which the bearing insert 55 slides. A peg 55b and a pair of stoppers 55c for preventing the disengagement of the bearing insert 56. The bearing surface 55a is curved in the anterior-posterior direction (A-P) and the traversal direction. Each curvature radius of the bearing surface 55a is virtually coincident with that of the unitary bearing insert, with the result the contact area is so large as to prevent local wear of polyethylene.

The unitary bearing insert 56 (FIGS. 22–24) enables highangle flexion. The posterior erect portion 1c (FIG. 19) effectively prevents the unitary bearing insert 56 from disengagement at a highly flexed state. The stoppers 55c (FIG. 25), which are extensions from the lateral sides of the tibial component 55 as viewed in a direction vertical to the longitudinal direction (A P), constrains the lateral displacement of the unitary bearing insert 56 and ensures prevention of the disengagement. Although not shown in FIGS. 25 and 26, the width (W) of the unitary bearing insert 56 (FIG. 2) is designed thoroughly shorter than the distance between a pair of the stoppers 55c, so that the bearing insert 56 can slide on the bearing surface 55a Although the stoppers 55c are inwardly curved in FIG. 25, they may be straight.

Figure 27A:
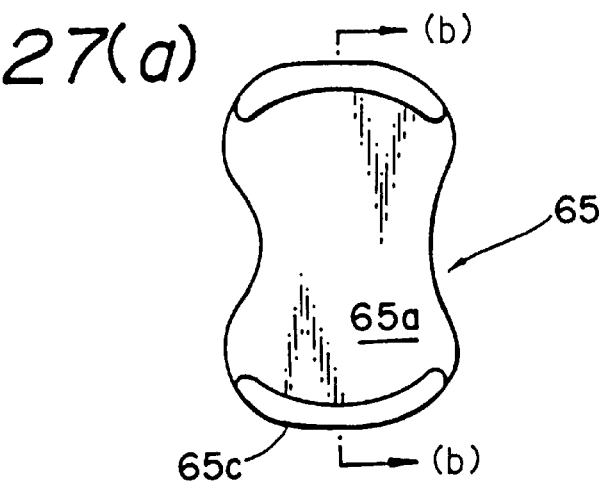
FIGS. 27(*a*) and 27(*b*) are drawings illustrating the tibial component of the unitary flat bearing-insert knee joint provided with extensions for guiding the bearing insert.
Figure 27B:
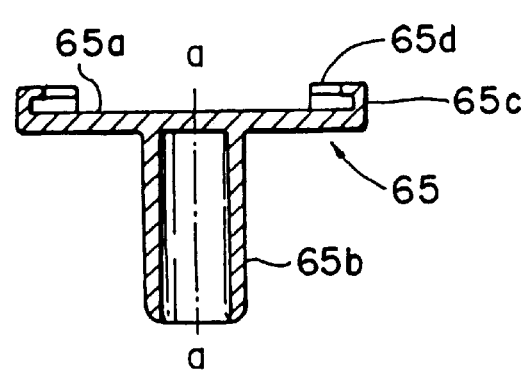
Figure 28:
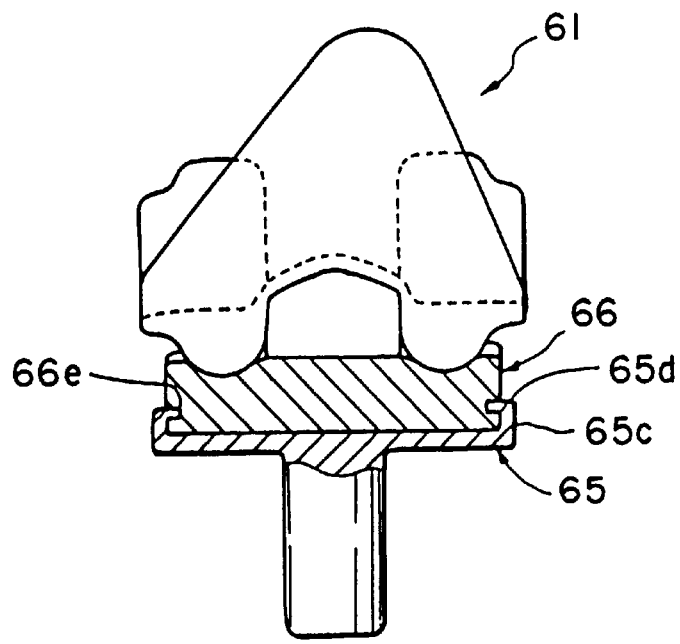
FIG. 28 is a front view of the unitary flat bearing insert knee-joint.

Referring to FIGS. 27 and 28, an embodiment of the unitary flat bearing-insert knee joint, which is additionally provided with a pair of stoppers, is illustrated. In this embodiment, the lower surface of the unitary bearing insert and the upper surface of the tibial component are flat. The tibial component 65 has a flat bearing surface 65a. The tibial component 65 has the stoppers 65c in the form of vertical extensions as in FIG. 25, and the vertical extensions are provided at the top end with inward lugs 65d. Meanwhile, the unitary bearing insert 66 has, on the lateral sides as shown in FIG. 28, grooves 66e extending in the longitudinal direction, for accommodating the lugs 65d thereinto. The unitary bearing insert 66 is, therefore, guided by the grooves 66e and the lugs 65c, and the disengagement of the bearing insert 66 is prevented. The structures 65c, 65d and 65e for preventing the disengagement can also be applied to the implant-metal knee joint.

As is described hereinabove, the prosthetic knee joint according to the present invention attains a higher degree of flexion than that attained by the conventional knee joint, and particularly attains high durability and stability due to a decrease in the wear of polyethylene.

We claim:

1. A prosthetic knee joint enabling high-angle flexion comprising:

a femoral component adapted to be secured to the distal femur, consisting of implant metal, having a first concave bearing surface adapted to be in slidable contact with a patella or a patellar component, a second concave bearing surface, a pair of spaced portions spaced by the first and second concave bearing surface, and forming an anterior erect portion, a lower portion and a posterior erect portion, which portions form a smoothly curved surface, and a swiveling shaft secured between a pair of the spaced portions at a posterior end;

a tibial component adapted to be secured to a proximal tibia, consisting of implant metal and having an upper surface provided with a peg; and, an intermediate unitary component consisting of polyethylene, held by the peg of said tibial component and having a central upheaval portion formed on an upper surface thereof and being in slidable contact with the second concave bearing surface in use, a pair of spaced curved bearing surfaces, in slidable contact with the femoral component in use, formed on an upper surface thereof and spaced by the central upheaval portion, a generally L shaped step formed adjacent to the upheaval portion, and a bore on the lower surface for accommodating the peg therein; the pair of spaced portions of the femoral bearing and the spaced curved surfaces of the intermediate unitary component form a sliding contact surface during flexion of the prosthetic knee joint, and said swiveling shaft and said generally L shaped step cooperate together to smoothly swivel the swiveling shaft during a high-angle flexion of the prosthetic joint, and said intermediate unitary component is posteriorly inclined, when it is positioned essentially at the center of the tibial component viewed in the direction of flexion, such that a virtual line connecting the anterior and posterior ends of the spaced portions of the femoral component extends beneath a horizontal line across the anterior end of said spaced portions.

2. A prosthetic knee joint according to claim 1, wherein the maximum depth of said first and second concave bearing surfaces are 10 mm or more.

3. A prosthetic knee joint according to claim 1 or 2, wherein the width of said first and second concave bearing surfaces measured by the distance between the apexes of the pair of the spaced portions is 58% or more of the width of the prosthetic knee joint.

4. A prosthetic knee joint according to claim 1 or 2, wherein said central upheaval portion has a generally concave configuration in the flexing direction.

5. A prosthetic knee joint according to claim 4, wherein said generally concave configuration has a more increased inclination in a rear side with the increase in the flexing angle.

6. A prosthetic knee joint according to claim 1 or 2, wherein said peg consists of a base portion, which has a diameter of from 5 to 30 mm and height of from 5 to 30 mm, and an upper portion, which has a diameter of from 1 to 10 mm and height of from 5 to 30 mm.

7. A prosthetic knee joint according to claim 1 or 2, wherein the generally L-shaped step comprises an erect portion, which slants inwardly in the direction of the swiveling shaft at an opening angle of less than 90°, and an arcuate basal surface having the curvature radius of approximately equal to the radius of the swivel axis.

8. A prosthetic knee joint according to claim 7, wherein the arcuate basal surface contacts with the arcuate region of swiveling axis $1j$ at a contact angle of 60° to 100°.

9. A prosthetic knee joint according to claims 1 or 2, wherein said peg provided on the upper surface of the tibial component consists of a base portion and an upper portion having smaller diameter than said base portion.

10. A prosthetic knee joint according to claim 9, wherein said intermediary unitary component comprises a bore, in which the base and upper portions of said peg are angular rotatively fitted.

* * * * *